United States Patent
Bjellqvist et al.

(10) Patent No.: US 9,063,082 B2
(45) Date of Patent: Jun. 23, 2015

(54) PRINTING OF ELECTROPHORESIS GELS

(75) Inventors: Bengt Bjellqvist, Stockhom (SE); Erik Bjerneld, Uppsala (SE); Jan-Olof Johansson, Uppsala (SE); Ronnie Palmgren, Uppsala (SE); Elsemarie Bjellqvist, legal representative, Uppsala (SE)

(73) Assignee: GE HEALTHCARE BIO-SCIENCES AB, Uppsala (SE)

( * ) Notice: Subject to any disclaimer, the term of this patent is extended or adjusted under 35 U.S.C. 154(b) by 79 days.

(21) Appl. No.: 13/512,354

(22) PCT Filed: Nov. 26, 2010

(86) PCT No.: PCT/SE2010/051306
§ 371 (c)(1),
(2), (4) Date: May 29, 2012

(87) PCT Pub. No.: WO2011/065909
PCT Pub. Date: Jun. 3, 2011

(65) Prior Publication Data
US 2012/0228121 A1    Sep. 13, 2012

(30) Foreign Application Priority Data

Nov. 27, 2009 (SE) .................................. 0950905

(51) Int. Cl.
*C08F 2/46* (2006.01)
*G01N 27/447* (2006.01)
*C07K 1/26* (2006.01)

(52) U.S. Cl.
CPC ............ *G01N 27/44747* (2013.01); *C08F 2/46* (2013.01); *C07K 1/26* (2013.01)

(58) Field of Classification Search
CPC .. G01N 27/44747; G01N 27/447; C08F 2/46; C07K 1/26
USPC ................... 204/456–470, 600–616
See application file for complete search history.

(56) References Cited

U.S. PATENT DOCUMENTS

| | | | |
|---|---|---|---|
| 4,189,370 A | 2/1980 | Boschetti | |
| 4,542,200 A * | 9/1985 | Nochumson | 526/238.2 |
| 4,840,756 A | 6/1989 | Ebersole et al. | |
| 5,427,729 A * | 6/1995 | Dubrow | 264/232 |
| 6,007,689 A | 12/1999 | Renfrew et al. | |
| 6,428,893 B1 * | 8/2002 | Barraud et al. | 428/392 |
| 2003/0006143 A1 | 1/2003 | Banerjee et al. | |

(Continued)

FOREIGN PATENT DOCUMENTS

| | | |
|---|---|---|
| JP | 2004077393 A | 3/2004 |
| JP | 2009042004 A | 2/2009 |
| WO | WO 2005/036153 | 4/2005 |
| WO | WO2010/115122 | * 10/2010 |

OTHER PUBLICATIONS

Machine translation JP 2009-042004, Dec. 6, 2013.*

(Continued)

*Primary Examiner* — Jennifer Dieterle (57) ABSTRACT

The invention relates to a method to produce gels for electrophoresis, wherein at least two monomer solutions are printed in a pattern on a substrate and the printed substrate is exposed to electromagnetic or ionising radiation so as to initiate polymerisation. The gels are useful for electrophoretic separation of proteins, peptides and/or nucleic acids.

17 Claims, 3 Drawing Sheets

(56) References Cited

U.S. PATENT DOCUMENTS

| | | | |
|---|---|---|---|
| 2003/0116437 A1 | 6/2003 | Burns et al. | |
| 2004/0255780 A1* | 12/2004 | Konig et al. | 95/266 |
| 2005/0168799 A1 | 8/2005 | Whitesides et al. | |
| 2009/0306769 A1* | 12/2009 | Schewe et al. | 623/1.34 |
| 2011/0056833 A1* | 3/2011 | Suzuki et al. | 204/466 |
| 2012/0129704 A1* | 5/2012 | Gunderson et al. | 506/2 |

OTHER PUBLICATIONS

BioRad Tech Note 1156 (2001).*
European Search Report Dated Feb. 6, 2014 Issued on Corresponding EP Application No. 10833671.0.

* cited by examiner

PRINTING OF ELECTROPHORESIS GELS

CROSS-REFERENCE TO RELATED APPLICATIONS

This application is a filing under 35 U.S.C. 371 of international application number PCT/SE2010/051306, filed Nov. 26, 2010, published on Jun. 3, 2011 as WO 2011/065909, which claims priority to application number 0950905-0 filed in Sweden on Nov. 27, 2009.

TECHNICAL FIELD

The present invention relates to the field of electrophoresis and more specifically to a method of preparing gels suitable for electrophoretic separation of proteins, peptides and/or nucleic acids. The invention also relates to electrophoresis gels and to kits for preparation of electrophoresis gels.

BACKGROUND OF THE INVENTION

Gel electrophoresis is a well established technique for the analysis of protein and nucleic acid preparations. In the most common way to carry out electrophoresis, a thin gel slab is cast in a mold, samples are applied at one end of the gel and an electric voltage is applied over the gel to make the sample molecules migrate electrophoretically in the field. The migration rate depends on the charge-to-mass ratios of the molecules as well as on their sizes, due to the sieving action of the gel medium. To improve the separation it is common to use gradient gels, where the solids content of the gel increases continuously in the migration direction. It is also common to introduce other spatial patterns in the gels, such as a sample application/stacking zone with lower solids content at the sample application end of the gel. In an alternative gel electrophoresis technique, isoelectric focusing (IEF), a pH gradient is formed over the gel and the sample molecules migrate electrophoretically to the point in the gradient where pH is equal to the isoelectric point of each molecule.

For high resolution gel electrophoresis, crosslinked polyacrylamide is the most common gel material. A casting solution of acrylamide (monomer), N,N'-methylene bisacrylamide (crosslinker), charged acrylamides (for IEF), buffer components, initiator components and optionally other components is poured or pumped into a mold and polymerization is initiated to convert the solution to a solid gel slab. A number of other monomer/crosslinker combinations can also be applied in a similar way. Monomer solutions of low viscosity are preferred to ensure easy and complete filling of narrow molds.

To create gradients, two casting solutions of different composition (typically differing in monomer concentration and/or monomer type) are mixed together by pumps or a special gradient mixer and the gradient solution is continuously pumped at low flow rate into one end of the mold. The mold is then filled with a casting solution having a gradient in the composition and, after polymerisation, a gradient gel slab will be formed. When a step change in gel composition is desired, such as for a sample application/stacking zone having lower concentration than the separation gel, it is more common to fill the mould with one casting solution (or a gradient), polymerize, fill the remaining mold space with another casting solution and then polymerise again. Both the gradient pumping and the double polymerization method are time-consuming and complicated to carry out and there is a need for more efficient methods.

JP2004007393 describes a non-contact ink-jet printer intended for application of agarose or polyacrylamide gels in patterns for electrophoresis. No details are however given on the formulation of the casting solutions. If standard polyacrylamide gel casting solutions are used with patterning techniques like this, no useful gels will be produced.

BRIEF DESCRIPTION OF THE INVENTION

One aspect of the present invention is to provide a convenient and reproducible method of manufacturing patterned electrophoresis gels from solutions of polymerisable monomers. This is achieved by printing at least two monomer solutions in a pattern on a substrate, and exposing the printed substrate to electromagnetic or ionising radiation so as to initiate polymerisation. In other words: at least two solutions, each of which comprises at least one polymerisable monomer, are spatially distributed over an open surface in a predetermined pattern and converted into a polymer gel pattern by polymerization using electromagnetic or ionising radiation.

Another aspect of the invention is to provide reproducible gels for electrophoresis. This is achieved by gels printed from at least two monomer solutions and polymerized using electromagnetic or ionising radiation.

A further aspect of the invention is to provide a convenient and reproducible way for users to prepare bespoke gels in the electrophoresis laboratory. This is achieved by a kit comprising at least one premixed monomer solution and an instruction comprising directions for printing the solution on a substrate and exposing the printed substrate to electromagnetic radiation so as to initiate polymerisation.

One or more of the aspects above may be achieved by the present invention as defined by the appended claims. Additional aspects, details and advantages of the invention will appear from the detailed description and claims that follow.

DEFINITIONS

The term "printing" herein means any method that distributes a liquid as a thin film over parts of an open substrate surface in a predetermined pattern. Non-limiting examples of printing techniques are: inkjet printing, intaglio printing, letterpress printing, flexo printing, pad printing, screen printing, gravure printing, lithographic printing, offset printing, xerographic printing, extrusion printing, pen printing, capillary tube printing or felt tip printing.

The term "monomer" herein means any polymerisable compound.

The term "thickener" herein means any compound that when incorporated in a liquid at a low concentration (such as below 10%) increases the viscosity of the liquid with at least a factor of five.

DETAILED DESCRIPTION OF THE INVENTION

In one embodiment of the present invention the radiation used to initiate polymerisation is either electromagnetic, i.e.

gamma ray, X-ray, ultraviolet, visible light, infrared or microwaves, or ionising radiation of a non-electromagnetic type, such as electron beam, ion beam, alfa radiation or beta radiation. An advantage of using radiation-initiated polymerisation is that stable monomer solutions can be used, with no need to mix in unstable redox or thermal initiators immediately before printing. In a specific embodiment, the radiation is light, such as ultraviolet light or short wavelength visible light. The ultraviolet light used can be UV-A (320-400 nm wavelength), UV-B (280-320 nm) or UV-C (100-280 nm). The light intensity can be 0.1-100 mW/cm$^2$, such as 1-20 mW/cm$^2$, and the irradiation time 1 s to 15 min, such as 0.5-5 min. An advantage of using light sources with predominantly UV-A and/or UV-B radiation is that they give even polymerisation through the depth of the monomer solution layer and that they need less safety shielding than sources with high UV-C intensity. An advantage of using light sources with less than 20 mW/cm$^2$ intensity is that heat-induced evaporation is not a problem. Fluorescent light tubes intended for suntanning or medical skin treatment can be used as light sources.

In one embodiment at least one of the monomer solutions comprises at least one photoinitiator. A photoinitiator is a chemical additive that initiates polymerisation upon irradiation with ultraviolet or visible light. Typically this involves free radicals generated either by fragmentation of the photoinitiator molecule or by hydrogen abstraction from a coinitiator molecule. In a specific embodiment the photoinitiator comprises an aromatic ketone. Examples of photofragmenting aromatic ketone photoinitiators are those selected from the group consisting of benzoin ethers, benzyl dimethyl ketal, 2-hydroxy-2-methylphenol-1-propanone, 2,2-diethoxyacetophenone, hydroxycyclohexyl phenyl ketone, 2- benzyl-2-N, N-dimethylamino-1-(4-morpholinophenyl) butanone, isonitrosopropiophenone and acetophenone derivatives. These initiators generally show a high efficiency, which is advantageous in that the tendency for atmospheric oxygen inhibition in the surface of the monomer solution layers is minimized, giving a more homogeneous gel. In a specific embodiment the initiator comprises an acetophenone derivative with a hydroxyl group in alfa position to the carbonyl carbon. Examples of hydrogen abstracting aromatic ketone photoinitiators are benzophenone and its derivatives, thioxanthone and its derivatives, fluorenone derivatives, dibenzosuberone derivatives, anthraquinone derivatives, phenanthrenequinones, camphorquinone and benzil with derivatives. Examples of coinitiators to be used with hydrogen abstracting photoinitiators include tertiary amines (e.g. N,N,N',N'-tetramethyl ethylenediamine (TEMED), triethanolamine, triethylamine etc.) and thiols (e.g. mercaptoethanol, dithiotreitol or dithioerythritol). In a specific embodiment the output spectrum of the light source is matched with the absorption spectrum of the photoinitiator so that a high fraction of the emitted light is absorbed by the initiator. This can e.g. be done by using a photoinitiator having a molar extinction coefficient higher than 200 liters*mole$^{-1}$*cm$^{-1}$ at the main emission peak wavelength of the light source. In a further embodiment the concentration of the photoinitiator is chosen so that the absorbance of the monomer solution (1 cm cuvette path length) is between 0.1 and 1.0 at the main emission peak wavelength in order to achieve both a high polymerization rate and a high penetration of the light through the depth of the monomer solution layer (giving uniform polymerization). An advantage of having a high polymerization rate is that the polymerization is less affected by oxygen inhibition at the open gel surface. Oxygen inhibition is a serious issue with conventional redox initiator systems like persulfate-TEMED. A general advantage of using photoinitiators is that the photoinitiator-containing monomer solutions can have a long shelf-life (years), provided that they are not exposed prematurely to ultraviolet or short-wave visible light.

In one embodiment the viscosity of at least one of the monomer solutions is at least 2, 4, 5 or 10 mPas (measured on a Brookfield rheometer at 25° C.), such as between 50 and 2000 mPas or between 100 and 1000 mPas. An advantage of increasing the viscosity above this level is that the printing pattern can be controlled (avoiding uncontrolled spreading or flow over the substrate surface). An increased viscosity will also decrease any oxygen inhibition effects on the polymerization. Further limits on the viscosity range may be set by the particular printing technique used. For some contemplated printing techniques, suitable viscosity ranges are: Inkjet printing 2-15 mPas, screen printing 100-2000 mPas, letterpress printing 50-2000 mPas, extrusion printing 50-1000 mPas.

According to one embodiment, at least one of the monomer solutions comprises a thickener. The function of the thickener is to increase the viscosity to the desired range, giving a suitable rheology (e.g. a "short" rheology with no tendency to string formation) and no negative effects on the electrophoresis or the detection of the separated biomolecules. The thickener may comprise a water soluble polymer (e.g. a polysaccharide) having a molecular weight and structure such that a 1% solution in water gives a viscosity of 5 mPas -20 000 mPas. In a specific embodiment the water soluble polymer is a non-ionic polysaccharide, optionally selected from the group consisting of non-ionic cellulose ethers, starch, starch derivatives and galactomannans. These polysaccharides have a rigid conformation giving generally high viscosities at low concentration; they are compatible with polyacrylamide gels (no precipitation phenomena during polymerisation) and they can be obtained with essentially no charged groups on the polymer (avoiding artefacts during electrophoresis). Specific examples of non-ionic cellulose ethers are hydroxyethyl cellulose, hydroxypropyl cellulose, methyl cellulose, ethylhydroxyethyl cellulose and methylhydroxyethyl cellulose. Specific examples of non-ionic starch derivatives are hydroxyethyl starch, hydroxypropyl starch, methyl starch, ethylhydroxyethyl starch and methylhydroxyethyl starch. Specific examples of non-ionic galactomannans are guar gum, hydroxypropyl guar gum and locust bean gum. In one embodiment the thickener solution or the thickener-containing monomer solution is filtered before use, so as to remove any particulates that can interfere with electrophoresis and detection.

In one embodiment at least one of the monomer solutions comprises a wetting agent. This reduces the surface tension and helps improving the homogeneity of the printed gels. The wetting agent can be a nonionic surfactant, such as a perfluorinated non-ionic surfactant. In a specific embodiment, the surface tension of at least one of the monomer solutions is less than 40 mN/m, such as less than 30 mN/m (measured by a du Nouy ring tensiometer).

In one embodiment at least one of the monomer solutions comprises a humectant. This reduces evaporation and helps improving the performance of the printed gels. The humectant can be a polyhydric alcohol like glycerol, ethylene glycol, propylene glycol, sorbitol, mannitol, sugars etc. Evaporation can also be reduced by controlling the humidity of the atmosphere during printing and polymerisation. In one embodiment the humectant is also used to regulate the viscosity of the monomer solutions.

In one embodiment at least one of the monomer solutions comprises at least one acrylic monomer, optionally selected from the group of acrylate esters, methacrylate esters, acrylamides and methacrylamides. Examples of acrylate and methacrylate esters include hydroxyalkyl esters like hydroxyethyl, hydroxypropyl and glyceryl (meth)acrylates, as well as PEG (meth)acrylates. Acrylamides and methacrylamides are hydrophilic monomers that are easily polymerised to hydrogels. The combination of acrylamide and N,N'-methylene bisacrylamide is commonly used in electrophoresis, but other acrylamide monomers are also contemplated, such as N,N-dimethylacrylamide, hydroxyalkyl acrylamides, N-isopropylacrylamide and charged acrylamide derivatives useful for preparation of immobilised pH gradients for isoelectric focusing (e.g. the Immobiline product range available from GE Healthcare, Sweden). As alternatives to N,N'-methylene bisacrylamide, N,N'-diallyltartardiamide, N,N'-1,2-dihydroxyethylene-bisacrylamide, N,N-bisacrylyl cystamine, trisacryloyl-hexahydrotriazine etc. can be used as crosslinking monomers. In one embodiment, at least one monomer is a macromonomer, which optionally may also function as a thickener. Contemplated macromonomers include acryl and vinyl derivatives of polyhydroxy polymers like polysaccharides, e.g. allyl dextran, allyl agarose or allylated cellulose derivatives.

In one embodiment the gel is a slab gel, i.e. an essentially planar, thin, essentially rectangular gel with a length-to-width ratio less than five. Such gels allow the application of several samples on the same gel, which also puts special demands on the quality of the printed gel pattern, e.g. homogeneous composition across the width of the gel, to avoid artefacts like waviness, smiling etc.

In one embodiment the print pattern comprises a total monomer concentration gradient. In sieving electrophoresis it can be advantageous to use a gel concentration gradient, typically within the 2-40% range, exemplified by the 8-25%, 8-18%, 4-15% and 10-15% gradients that have been found useful for common protein size ranges. Gradients with total monomer concentration 2-10% at the low concentration end and 10-40% at the high concentration end are contemplated. The gradients may be linear or non-linear, e.g. with exponential, parabolic or hyperbolic concentration profiles, and they may in addition contain one or more step gradients. A continuous gradient can also be approximated by a series of small step gradients.

In another embodiment the print pattern comprises a monomer type gradient. This means that the composition of monomers at one end of the gradient is different from the composition of monomers at the other end of the gradient. One example of such a gradient is an immobilised pH gradient prepared with charged acrylamides (e.g. Immobiline products) and another example is a crosslink density gradient for sieving electrophoresis, using e.g. a gradient in the N,N'-methylene bisacrylamide-acrylamide monomer ratio. The monomer type gradients can also be linear or non-linear, e.g. with exponential, parabolic or hyperbolic concentration profiles, and they may in addition contain one or more step gradients. It is also possible to create gradients with respect to both monomer type and monomer concentration.

In one embodiment the substrate material for the printed gels is a polymeric material. It can be a transparent or non-transparent plastic film, a porous membrane or a fibrous material (paper, nonwoven etc). The support material may be coated with a layer promoting adhesion to the gel and it may also comprise functional layers, e.g. metal layers. In an alternative embodiment the substrate material is inorganic, such as glass plate or a ceramic.

In certain embodiments the substrate material has a hydrophilic surface, e.g. giving an equilibrium water contact angle of less than about 60°, such that less than about 40°, less than about 30° or less than about 20° as measured with pure water by the well known sessile drop method using e.g. a Ramé Hart contact angle goniometer. An advantage of using a hydrophilic substrate surface is that thickness and pattern inhomogeneities in the gel can be avoided. In a specific embodiment the substrate material is a plastic film coated with a hydrophilic layer, such as a polysaccharide derivative, e.g. allyl agarose as in the commercially available product GelBond PAG (Lonza). The hydrophilic side of GelBond PAG has a water contact angle of 14°, while the untreated backside has a water contact angle of 67°. The substrate can also be a clean glass surface, which will have a water contact angle of less than 20°.

In one embodiment the monomer solutions are printed on a moving substrate, such as a continuous web from a roll. This is particularly advantageous for high volume production, where the monomer solution pattern can be printed on e.g. a support film from a roll and the printed film can be continuously conveyed to an irradiation zone for polymerization. After polymerization, the moving film-gel composite may be cut into individual gels and packaged.

In one embodiment the thickness of the polymerized gel layer is higher than 50 microns, such as 100-1000 microns or 200-600 microns.

In one embodiment the printed pattern is formed by contacting different areas of the substrate with different monomer solutions, i.e. each substrate area segment is only contacted once with a monomer solution. This embodiment initially produces step gradients, although interdiffusion before polymerization may smoothen out the steps to some extent. For complex patterns like gradients (approximated e.g. by a series of several small step gradients), a large number of different monomer solutions may be required. Typically more than four, such as 5-50 or 8-40, different monomer solutions are applied. In an alternative embodiment the printed pattern is formed by contacting area segments of the substrate with several different monomer solutions in sequence. In this embodiment the local solution composition in each spot will essentially be a weighted average of the different compositions applied to that particular spot. Complex patterns like e.g. gradients can be formed from only two different monomer solutions, applied in different amounts to different substrate area segments. Typically, two to four different monomer solutions are applied in this embodiment. Multilayer gel constructs are also contemplated, where one type of gel is deposited on top of another.

In one embodiment the monomer solutions are extrusion printed through a multitude of nozzles. At least two monomer solutions are fed through at least two nozzles in close proximity to the substrate surface. The pattern is formed as the nozzles and the substrate surface move in relation to each other. According to one embodiment the nozzles are fixed in a nozzle assembly while the substrate surface moves and according to an alternative embodiment the substrate surface is fixed while the nozzles move over the substrate in a controlled way. The nozzles can be tubular with e.g. circular, ellipsoidal or rectangular cross-section and they may be tapered, e.g. with openings narrower than the main part of the tubular structures. The nozzle ends can be cut perpendicular or at an angle relative to the length axis of the tubular structures. In one embodiment the nozzles are held in a fixture forming a straight line of nozzles with the ends 0.1-3 mm above the substrate surface. The monomer solutions are fed through the nozzles, using e.g. a multichannel pump and a striped pattern of monomer solutions is formed on the substrate due to the relative movement. Some time is allowed for leveling of the monomer film (and for some interdiffusion between the different monomer solutions, if desired) and then the film pattern is irradiated and polymerized. Leveling will typically take place within seconds, while interdiffusion may require minutes.

In one embodiment the monomer solutions are printed by screen printing. A porous screen is partially coated with a masking material and is brought into contact with the substrate surface. A monomer solution is applied to the screen so that it passes through the non-masked areas of the screen and wets the corresponding accessible substrate surface areas. A second screen with a different pattern of masked and non-masked areas is then brought into contact with the substrate surface and a second monomer solution is applied. The process may be repeated with further screens and monomer solutions. Irradiation and polymerization may take place either directly after the application of each monomer solution or once the substrate has been contacted with all the monomer solutions.

In one embodiment the monomer solutions are printed by letterpress printing. A printing plate with elevated printing areas and recess non-printing areas is supplied. A monomer solution is applied to at least the printing areas and the plate is brought into contact with the substrate surface so that the monomer solution transfers to the areas in contact with the printing areas. A second printing plate with a different pattern of printing and non-printing areas is then supplied, coated with a second monomer solution and brought into contact with the substrate surface. The process may be repeated with further plates and monomer solutions. Irradiation and polymerization may take place either directly after the application of each monomer solution to the substrate or once the substrate has been contacted with all the monomer solutions.

In one embodiment the monomer solutions are printed by inkjet printing. Small droplets of a monomer solution are sprayed from a nozzle onto the substrate surface in a controlled pattern. Then droplets of a second monomer solution are sprayed through a second nozzle onto the substrate surface in a different controlled pattern. The process may then be repeated with further nozzles and monomer solutions. Irradiation and polymerization may take place either directly after the spraying of each monomer solution or once the substrate has been sprayed with all the monomer solutions.

In one embodiment the monomer solutions are printed by contact printing. Contact printing (as opposed to non-contact printing) is a general term for methods where a printing head, nozzle, plate, pad, screen etc is brought into contact with the substrate surface either directly (solid-solid contact) or via a liquid bridge (solid-liquid-solid contact). One advantage of using contact printing is that monomer solutions of higher viscosities can be used, allowing for better consistency in the pattern formation on the substrate surface. This applies particularly when higher film thicknesses, such as over 100 microns, are desired. Examples of contact printing methods are intaglio printing (plate with recesses filled with monomer solution), letterpress printing (plate with elevated areas wetted by monomer solution), flexo printing (flexible plate with elevated areas wetted by monomer solution), pad printing (pad to which monomer solution has been transferred in selected printing areas only), screen printing (screen with non-masked areas where monomer solution is brought into contact with substrate surface), gravure printing (plate with recesses filled with monomer solution), lithographic printing (plate with hydrophilic areas selectively wetted by monomer solution), offset printing (plate/web to which monomer solution has been transferred in selected printing areas only), extrusion printing (nozzles brought into contact with the substrate surface via a continuous monomer solution liquid bridge), pen printing (tubular structure brought into contact with the substrate surface either directly or via a continuous monomer solution liquid bridge), capillary tube printing (tubular structure brought into contact with the substrate surface either directly or via a continuous monomer solution liquid bridge) and felt tip printing (porous tip brought into contact with the substrate surface either directly or via a continuous monomer solution liquid bridge).

One embodiment is a kit comprising at least one premixed monomer solution and an instruction comprising directions for printing the solution on a substrate and exposing the printed substrate to electromagnetic radiation so as to initiate polymerisation. If the end-user of the electrophoresis gels has a printer, he can conveniently make bespoke gels for his own specific separation needs. It will then be an advantage if the gel solutions are supplied in the form of a kit with an instruction on the gel preparation from these specific solutions. In one embodiment the monomer solution is packed in a cartridge designed for direct mounting in a printer. One advantage of this is that the end-user will not be exposed to toxic acrylamide or other monomers during preparation of the gels.

In one embodiment the invention comprises a kit with at least one premixed monomer solution and an instruction comprising directions for printing the solution on a substrate and exposing the printed substrate to electromagnetic radiation so as to initiate polymerisation. In one embodiment the instructions comprise directions for using a printer specifically designed for manufacture of electrophoresis gels. In another embodiment the kit comprises a support material for printing monomer solutions. This material may be of a type and shape specifically designed for electrophoresis gels.

Other features and advantages of the invention will be apparent from the following examples and from the claims.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

EXAMPLES

Example 1 Extrusion Printing

Example 1a

Extrusion Printing Equipment

Figure 1:
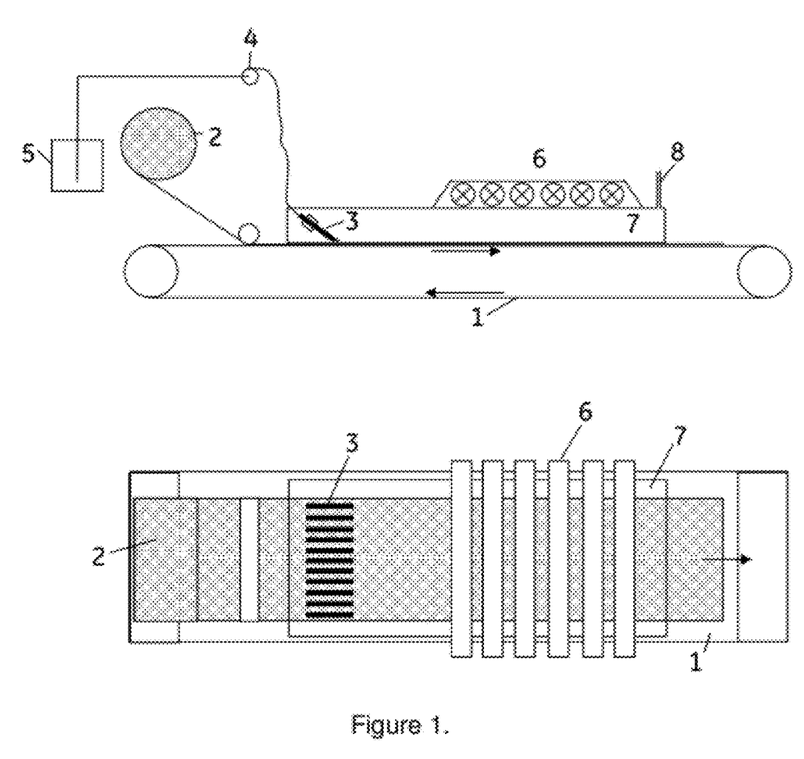
FIG. 1 shows a general setup for extrusion printing.

The general setup for extrusion printing is shown in FIG. 1. A conveyor belt (1) of length 2.5 m and width 20 cm is driven with constant speed and with essentially no vibrations using an electric motor and a worm gear. The line speed can be continuously varied between 0.25 and 4.5 cm/s. A roll (2) of support film (GelBond PAG from Lonza) of width 125 mm, length 240 m is suspended above the belt and the film is pressed onto the belt with a steel roll (during start-up, the lead of the film is taped to the belt). A support for the extrusion nozzles (3) is mounted on the frame of the belt conveyor and a transparent plastic box (7) of UV-transparent Plexiglas acrylic is fixed over the belt to provide a possibility for inert gas application during printing and polymerization. The plastic box has a gas inlet (8), a gas distributor and baffles to provide an efficient gas flow counter-current to the belt movement during printing.

Figure 2:
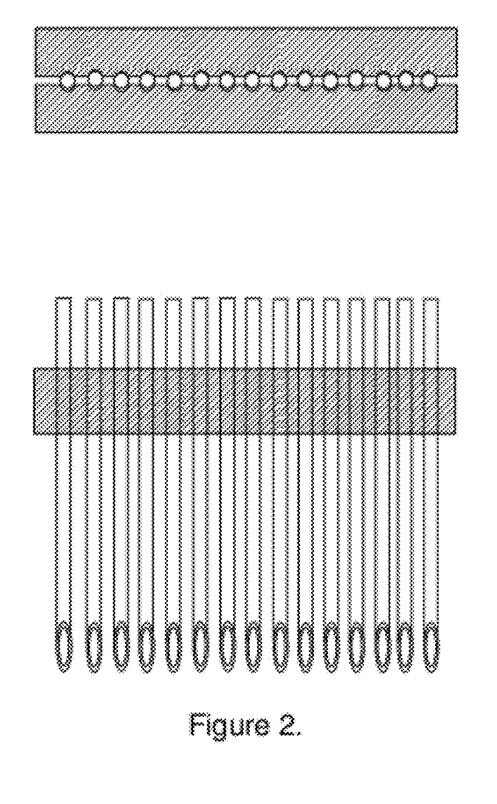
FIG. 2 shows a nozzle assembly for extrusion printing.

The nozzles (also shown in detail in FIG. 2) are fed with monomer solutions from solution reservoirs (5) using either a 16-channel peristaltic pump (4) or a 4-channel piston pump. The rate of the pump is controlled by an LCC-500 liquid chromatography control unit from Pharmacia Biotech AB, Sweden.

Polymerisation is accomplished by UV irradiation using six Philips TL/12 suntanning fluorescent light tubes (6). These have an output of 4.35 mW/cm2 UV-A, 13.8 mW/cm2 UV-B and 0.01 mW/cm2 UV-C radiation. A typical irradiation time is about 3 min, giving a reasonable length of the irradiation zone at convenient line speeds.

Example 1b

Extrusion Printing

According to general polyacrylamide electrophoresis terminology, the monomer concentrations are denoted as T (%)=acrylamide+N,N'-methylene bisacrylamide (g) per 100 g water and C=N,N'-methylene bisacrylamide (g) per 100 g acrylamide+N,N'-methylene bisacrylamide.

Solutions:
Buffer stock (10 ×): 1.18 M Tris/HAc pH 6.40 with 1% SDS (sodium dodecyl sulfate)
Monomer stock T40 C2: 392 g acrylamide and 8.0 g N,N'-methylene bisacrylamide are dissolved in 1000 ml distilled water.
Monomer stock T10 C3: 97 g acrylamide and 3.0 g N,N'-methylene bisacrylamide are dissolved in 1000 ml distilled water.
Initiator stock 100 mM: 2.04 g Irgacure 184 (Ciba Specialty Chemicals) is dissolved in 100 ml ethylene glycol.
Wetting agent stock: 5 g Fluorad FC-430 (nonionic perfluorinated surfactant from 3M) is dissolved in 95 ml distilled water.
Stacking gel solution T6 C3: 300 ml T10 C3 stock, 50 ml buffer stock, 10 ml initiator stock, 5 ml wetting agent stock, 35 ml distilled water and 100 ml glycerol are mixed. 2.00 g Natrosol HHX (Aqualon) is dissolved in the mixture.
T8 C2 solution: 200 ml T40 C2 stock, 100 ml buffer stock, 20 ml initiator stock, 10 ml wetting agent stock, 470 ml distilled water and 200 ml glycerol are mixed. 4.00 g Natrosol HHX (Aqualon) is dissolved in the mixture.
T18 C2 solution: 4500 ml T40 C2 stock, 100 ml buffer stock, 20 ml initiator stock, 10 ml wetting agent stock, 220 ml distilled water and 200 ml glycerol are mixed. 4.00 g Natrosol HHX (Aqualon) is dissolved in the mixture.

13 monomer solutions were prepared according to Table 1. The values of T (monomer concentration) and C (crosslinker content) in the different solutions were as listed in Table 1. The viscosities of the monomer solutions were approx 300 mPas and the surface tensions approx. 35 mN/m.

TABLE 1

| Syringe no. | T6 C3 solution (ml) | T8 C2 solution (ml) | T18 C2 solution (ml) | Resulting T (%) | Resulting C (%) |
|---|---|---|---|---|---|
| 1 | 100 | — | — | 6 | 3 |
| 2 | 100 | — | — | 6 | 3 |
| 3 | 100 | — | — | 6 | 3 |
| 4 | 100 | — | — | 6 | 3 |
| 5 | 100 | — | — | 6 | 3 |
| 6 | 100 | — | — | 6 | 3 |
| 7 | 100 | — | — | 6 | 3 |
| 8 | 100 | — | — | 6 | 3 |
| 9 | 100 | — | — | 6 | 3 |
| 10 | 100 | — | — | 6 | 3 |
| 11 | — | 100 | — | 8 | 2 |
| 12 | — | 100 | — | 8 | 2 |
| 13 | — | 90.9 | 9.1 | 8.91 | 2 |
| 14 | — | 90.9 | 9.1 | 8.91 | 2 |
| 15 | — | 81.8 | 18.2 | 9.82 | 2 |
| 16 | — | 81.8 | 18.2 | 9.82 | 2 |
| 17 | — | 72.7 | 27.3 | 10.73 | 2 |
| 18 | — | 72.7 | 27.3 | 10.73 | 2 |
| 19 | — | 63.6 | 36.4 | 11.64 | 2 |
| 20 | — | 63.6 | 36.4 | 11.64 | 2 |
| 21 | — | 54.5 | 45.5 | 12.55 | 2 |
| 22 | — | 54.5 | 45.5 | 12.55 | 2 |
| 23 | — | 45.5 | 54.5 | 13.45 | 2 |
| 24 | — | 45.5 | 54.5 | 13.45 | 2 |
| 25 | — | 36.4 | 63.6 | 14.36 | 2 |
| 26 | — | 36.4 | 63.6 | 14.36 | 2 |
| 27 | — | 27.3 | 72.7 | 15.27 | 2 |
| 28 | — | 27.3 | 72.7 | 15.27 | 2 |
| 29 | — | 18.2 | 81.8 | 16.18 | 2 |
| 30 | — | 18.2 | 81.8 | 16.18 | 2 |
| 31 | — | 90.9 | 9.1 | 17.09 | 2 |
| 32 | — | 90.9 | 9.1 | 17.09 | 2 |
| 33 | — | — | 100 | 18 | 2 |
| 34 | — | — | 100 | 18 | 2 |
| 35 | — | — | 100 | 18 | 2 |
| 36 | — | — | 100 | 18 | 2 |

Figure 3:
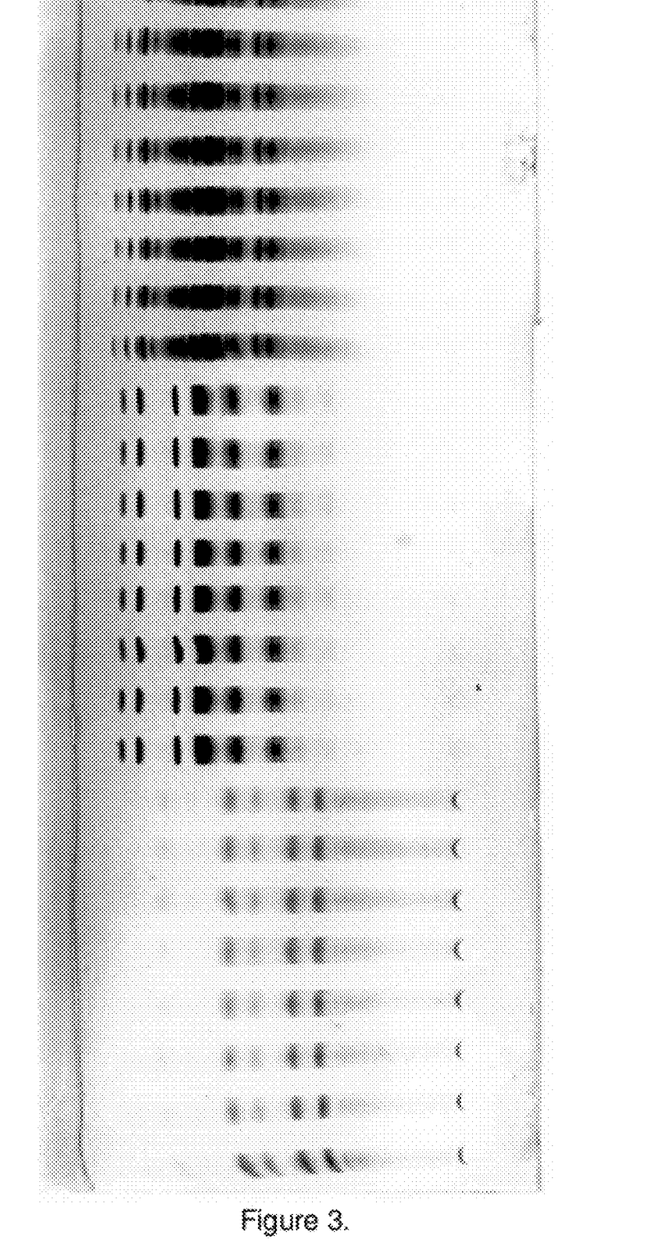
FIG. 3 shows an electrophoresis gel prepared by extrusion printing, after separation of test proteins by SDS-PAGE and silver staining. Lanes 1-8 E Coli extract, lanes 9-16 GE Healthcare LMW-SDS Marker kit, lanes 17-24 GE Healthcare HMW-SDS Marker kit.

The solutions were pumped with a multichannel peristaltic pump (pump rate 0.9 ml/min per syringe) through a nozzle setup consisting of 36 1.8 mm hypodermic syringes flattened at the sharp end using a vice and mounted evenly in a 110 mm line. The nozzles were placed over a moving web of 125 mm wide GelBond PAG support film (line speed 50 cm/min) and after the printing zone, the web moved through the irradiation zone (irradiation time approx. 1 min) A 25 cm length of the gel was cut out and run under standard SDS electrophoresis conditions with GE Healthcare protein markers (HMW and LMW) and an *E Coli* extract as test proteins. After electrophoresis, the gel was silver stained. As FIG. 3 shows, a good electrophoresis result with good homogeneity across the gel was obtained.

Example 1c

Extrusion Nozzles

Setup 1: 16 1.4 mm hypodermic syringes were flattened at the sharp end using a vice. They were then mounted evenly in a 50 mm line.

Setup 2: 16 4.0 mm stainless steel tubes were machined to give 0.5 mm wall thickness at the end and the ends were then flattened using a vice. They were mounted evenly in a 110 mm line.

Setup 3: 36 1.8 mm hypodermic syringes were flattened at the sharp end using a vice. They were then mounted evenly in a 110 mm line.

Setup 4: A flat rectangular steel conduit of width 110 mm and height 2 mm was prepared, having divider bars to provide 32 rectangular channels of width 3 mm and height 2 mm All these nozzle setups were tested for printing of acrylamide-BIS monomer solution as in Example 1 b). The pump speed was carefully controlled to give the same fluid velocity in the nozzle as the band/support film velocity. It was found that the flattened syringes of setups 1 and 3 gave the best gels.

Example 1d

Influence of Oxygen

Sparging of the monomer solutions with argon improved the polymerization and the gels thus produced had sharper protein bands. When light sources with less efficiency than the Philips TL/12 tubes were used, it was also necessary to provide a flow of argon or nitrogen through the plastic box during irradiation to get complete polymerization also on the gel surface.

Example 1e

Photoinitiators

A number of more or less water soluble photoinitiators were tested:
Irgacure 184 (1-Hydroxy-cyclohexyl-phenyl-ketone,Ciba Specialty Chemicals)
Irgacure 907 (2-Methyl-1[4-(methylthio)phenyl]-2-morpholinopropan-1-one, Ciba Specialty Chemicals)
Irgacure 651 (2,2-Dimethoxy-1,2-diphenylethan-1-one, Ciba Specialty Chemicals)
Irgacure 2959 (1-[4-(2-Hydroxyethoxy)-phenyl]-2-hydroxy-2-methyl-1-propane-1-One, Ciba Specialty Chemicals)
Darocur 1173 (2-Hydroxy-2-methyl-1-phenyl-propan-1-one, Ciba Specialty Chemicals)
Quantacure QTX (2-hydroxy-3-(3,4-dimethyl-9-oxo-9H-thioxanthen-2-yloxy)-N,N,N-trimethyl-1-propanaminium chloride, Ward Blenkinsop)+N,N,N',N'-tetramethyl-ethylenediamine The most efficient photoinitiator was Irgacure 184, followed by Darocur 1173 (both are acetophenone derivatives with a hydroxyl group in alfa position to the carbonyl carbon). These are not nominally water soluble, but 100 mmol/l stock solutions can be prepared in ethylene glycol and used to give 1-10 mmol/l working concentration in the aqueous monomer solutions. No precipitation phenomena are observed under these conditions.

Example 1f

Thickeners

A number of polymeric water-soluble thickeners were tested:
Hydroxyethyl cellulose (Natrosol 250HHR, 250HHBR and 250HHX from Hercules). Tested in concentrations 0.3-0.6 g/100 ml. The solutions were filtered to remove fibrous residues. Gels printed from monomer solutions with 0.44 g/100 ml gave very sharp protein bands. 250HHX dissolved faster than the other two grades, which is advantageous.

Potato starch Mw 2 kDa (Trecomex AET-4 from Lyckeby Stärkelsen, Sweden). Tested in concentrations 0.9-2.5 g/100 ml. The protein bands were relatively sharp, but a dark background was formed in silver staining—presumably due to the presence of colloidal particles in the Trecomex solution.

Waxy maize starch, 99% amylopectin (Firmtex from National Starch and Chemical Co.). Tested in concentrations 2-3 g/100 ml. Gels printed from monomer solutions with 2.4 g/100 ml gave reasonably good results.

Hydroxypropyl cellulose (Klucel HF from Hercules). Tested in concentrations 0.3-0.5 g/100 ml.

Gels printed from monomer solutions with 0.44 g/100 ml were very loose and the protein bands stopped migrating prematurely.

Carboxymethyl cellulose (Blanose from Hercules). Tested in 0.44 g/100 ml concentration. Performed well in SDS electrophoresis, but shifted the pH gradient in isoelectric focusing—presumably due to the presence of the charged carboxylate groups.

Linear polyacrylamide (Superfloc N300 from Cytec). Tested in concentrations 0.23-2 g/100 ml. 1 g/100 ml concentration was needed to get sufficient viscosity, but these monomer solutions were very stringy. The protein migration pattern was satisfactory, although the gels swelled considerably during staining.

Polyethylene oxide Mw $5*10^6$ Da (Polyox coagulant, Union Carbide). Gave very stringy solutions.

Control experiments without thickener did not produce any useful gels. The gels were inhomogeneous, with thickness variations and severely deformed gradient patterns.

Example 2 Inkjet Printing

Gels were cast in various patterns using a Dimatix DMP2831 printer (Fujifilm). The printhead uses a drop volume of 10 pl. Glycerol was added to the casting solution to achieve a suitable viscosity in the range 2-15 mPas, a viscosity of 4 mPas produced good results. An example of a gel recipe which produced well defined patterns of gels is:
12.5 ml 1.5 M tris-Cl buffer pH 8.6
17.5 ml 85% glycerol
1.5 ml 100 mM Irgacure 184 in ethylene glycol
4.5 ml N,N di-methylacrylamide
4.5 ml N,N' methylenebisacrylamide 2% (w/v)
9.5 ml $H_2O$ The amount of monomer and cross-linker in the recipe was varied and the different recipes produced well defined gel patterns.

Prior to filling the printer head, the casting solution was filtered using a 13 mm syringe filter (0.45 μm pore size, PTFE). The fluid was deposited on glass and plastic substrates treated with different adhesive layers. We found that non-treated hydrophilic clean glass surfaces and the hydrophilic treated side of GelBond PAG plastic films were suitable substrates for printing. Hydrophobic surfaces, such as the untreated polyethylene terephthalate backside of GelBond PAG, did not produce acceptable patterns. Depending on the pattern, different number of layers (typically 2-4 layers) and different drop spacing were used.

After the deposition the fluid was illuminated using a Vilber Lourmat UV-lamp (VL-208BL 2×8 W, 365 nm, power 2 mW/cm$^2$) and illumination times in the range 2-10 min. Various channels were printed; width range 0.1 to 4 mm, in lengths up to 60 mm Both single and parallel channels (2 mm pitch) were made. The estimated thickness of a wet layer is in the range 10-20 μm. We also made various sample loading zones and contact zones for electrophoresis buffer pads and electrodes. To test both that a gel had formed and the gel adhesion to the substrate the gel was washed in water. This allows rehydration with a suitable electrophoresis buffer.

All patents, patent publications, and other published references mentioned herein are hereby incorporated by reference in their entireties as if each had been individually and specifically incorporated by reference herein. While preferred illustrative embodiments of the present invention are described, one skilled in the art will appreciate that the present invention can be practiced by other than the described embodiments, which are presented for purposes of illustration only and not by way of limitation. The present invention is limited only by the claims that follow.

The invention claimed is:

1. A method of producing gels for electrophoresis, providing a printed substrate and exposing a printed substrate to electromagnetic or ionising radiation for sufficient time to initiate polymerisation; wherein more than four different monomer solutions are printed in a pattern on a substrate to provide said printed substrate and wherein the monomer solutions are extrusion printed through a multitude of nozzles.

2. The method of claim 1, wherein the radiation is ultraviolet light.

3. The method of claim 1, wherein at least one of the monomer solutions comprises at least one aromatic ketone photoinitiator.

4. The method of claim 1, wherein the viscosity of at least one of the monomer solutions is 50-1000 mPas.

5. The method of claim 1, wherein at least one of the monomer solutions comprises a thickener.

6. The method of claim 5, wherein the thickener comprises a non-ionic polysaccharide.

7. The method of claim 5, wherein the thickener is selected from the group consisting of non-ionic cellulose ethers, starch, starch derivatives and galactomannans.

8. The method of claim 1, wherein at least one of the monomer solutions comprises at least one acrylic monomer.

9. The method of claim 1, wherein at least one of the monomer solutions comprises acrylamide and N,N'-methylenebisacrylamide.

10. The method of claim 1, wherein the gels are slab gels.

11. The method of claim 1, wherein the print pattern comprises a total monomer concentration gradient.

12. The method of claim 1, wherein the print pattern comprises a monomer type gradient.

13. The method of claim 1, wherein the monomer solutions are printed on a moving substrate.

14. The method of claim 1, wherein the substrate material for the printed gel has an equlibrium water contact angle of less than about 60°.

15. The method of claim 5, wherein the thickener comprises a water soluble polymer having a molecular weight and structure such that a 1% solution in water gives a viscosity of 5 mPas-20 000 mPas.

16. The method of claim 1, wherein at least one of the monomer solutions comprises a wetting agent.

17. The method of claim 1, wherein the substrate material for the printed gel is a plastic film coated with a polysaccharide derivative.

* * * * *